(12) United States Patent
McKendry et al.

(10) Patent No.: US 6,932,790 B2
(45) Date of Patent: Aug. 23, 2005

(54) ADAPTER FOR HUMAN BREAST PUMPS

(75) Inventors: Bruce McKendry, Benecia, CA (US); Sung Lee, Elk Grove, CA (US)

(73) Assignee: L. Jason Clute, Alamo, CA (US)

( * ) Notice: Subject to any disclaimer, the term of this patent is extended or adjusted under 35 U.S.C. 154(b) by 0 days.

(21) Appl. No.: 10/625,246

(22) Filed: Jul. 23, 2003

(65) Prior Publication Data

US 2005/0020971 A1 Jan. 27, 2005

(51) Int. Cl.[7] .............................................. A61M 1/06
(52) U.S. Cl. ....................................................... 604/74
(58) Field of Search .............................. 604/73–76, 310, 604/312, 313, 315–324, 346; 417/415

(56) References Cited

U.S. PATENT DOCUMENTS

| | | | |
|---|---|---|---|
| 4,263,912 A | * | 4/1981 | Adams ......................... 604/75 |
| 4,607,596 A | | 8/1986 | Whittlestone et al. |
| 4,857,051 A | * | 8/1989 | Larsson ........................ 604/74 |
| 5,514,166 A | * | 5/1996 | Silver et al. .................. 604/74 |
| 5,542,921 A | * | 8/1996 | Meyers et al. ................ 604/74 |
| 6,042,560 A | * | 3/2000 | Niederberger ................ 604/74 |
| 6,257,847 B1 | * | 7/2001 | Silver et al. ................ 417/415 |
| 6,706,012 B2 | * | 3/2004 | McKendry et al. ........... 604/74 |

FOREIGN PATENT DOCUMENTS

| | | |
|---|---|---|
| EP | 1 163 915 | 12/2001 |

* cited by examiner

*Primary Examiner*—Nicholas D. Lucchesi
*Assistant Examiner*—Michael M. Thompson
(74) *Attorney, Agent, or Firm*—Greer, Burns & Crain, Ltd.

(57) ABSTRACT

An air circuit is disclosed that communicates with a cycling, bi-directional or intermittent pressure source, splitting the output of the pressure source into two channels. One channel continues to cycle bi-directional or intermittent pressure, and a second channel employs a one-way valve allowing output of vacuum only. In one embodiment, this circuit can be used to actuate unidirectional, pulsating human breast milk expression devices that use vacuum to draw milk, while massaging the breast with pulsating pressure. The air circuit preferably includes an additional one-way valve, which is located upstream of the one-way negative pressure valve, for relief of excess positive pressure within the circuit. The negative channel output of the air circuit can contain a pressure regulation apparatus for end-user control of negative pressure to the expression devices.

7 Claims, 7 Drawing Sheets

ADAPTER FOR HUMAN BREAST PUMPS

This invention relates to adapters for human breast pumps, and more particularly, to methods and apparatus for operating a lined breast cup kit that requires both pulsating pressure and a separate vacuum source, using a pump having an intermittent or bi-directional pressure source.

BACKGROUND OF THE INVENTION

Breast milk can be pumped by human breast pumps, typically with flanges that are pressed to the breasts, as seen in FIG. 6A. In FIG. 6A, a flange 600 is in operable communication with a breast pump 602 that produces pressure intermittently, or cyclically in both the positive and negative aspects, as seen in FIG. 6B. Negative pressure, or vacuum, withdraws the milk, which falls through a tube 603 into a container 604. This process, commonly described as suck and release, is the underlying mechanical means of milk extraction employed by most conventional human breast pumps.

A different breast milk expression device is disclosed in U.S. Pat. No. 4,607,596, issued Aug. 26, 1986, to Whittlestone et al. As seen in FIG. 7A, the Whittlestone apparatus 700 has two breast cups 702, 704 which each have a liner 706, 708 respectively. Each liner creates a pulsation chamber 710 between the liner and the cup, and a vacuum chamber 712 inside the liner when a breast is placed in the cup.

A pump 714 provides vacuum through lines 716, 718 and pulsating pressure through lines 720, 722, to the inner and outer chambers 712, 710, respectively, as seen in FIG. 7B. The line 712V in FIG. 7B shows the generally constant vacuum at the breast in the chamber 712, and the line 710P shows the pulsation pressure in the chamber 710. Thus, the Whittlestone device is distinguished from the other devices by utilizing unidirectional negative pressure for primary milk extraction, in combination with a pressure chamber that utilizes alternating positive and negative pressure to actuate pulsation (liner wall movement, ISO 3918) to express milk in a manner both effective and comfortable for the user.

Suck and release breast pumps, along with their flanges, are owned by or available to many women, retail, rental and medical facilities. However, these pumps could not be used with the Whittlestone breast cup assemblies because the Whittlestone breast cup assemblies require two types of pneumatic power. Thus, there is a need for an adapting device that permits the suck and release pumps to actuate breast cup kits requiring dual sources of pressure.

Accordingly, an object of the present invention is to enable use of breast cup assemblies that utilize dual pressure sources, such as negative unidirectional pressure for vacuum to the breast, and bidirectional pressure for actuation of pulsation, in combination with single pressure output suck and release breast pumps.

SUMMARY OF THE INVENTION

In keeping with one aspect of the invention, an air circuit provides for the utilization of a motorized or manual suck and release breast pump in combination with the previously incompatible technology embodied in devices requiring dual pressure sources, one unidirectional in the negative, and the other bi-directional. Such devices typically have a liner secured in a breast cup to create a pulsation chamber between the cup and liner, and a vacuum chamber inside the liner when a breast is placed in the cup. The assembly of the cup, liner and a collection vessel is sometimes called an express kit, i.e., a kit for the extraction or expression of milk from the breast.

The air circuit attaches to the pressure output of a suck and release breast pump, routing, or splitting, the pressure output into two channels, described herein as Outputs P (for bidirectional or intermittent pulsation pressure) and V (for unidirectional vacuum pressure), respectively. Output P has a tubular channel communicating pulsation pressure from the source to the pulsation pressure chamber of at least one express kit.

Output V includes a tubular channel communicating negative (vacuum) unidirectional pressure only to the vacuum outlet of the express kit, the vacuum outlet being in communication with the nipple of the breast. Output V includes a one-way directional valve, allowing the output of only unidirectional negative pressure for communication with the vacuum outlet of the express kit.

In one embodiment according to the present invention, a second one-way directional valve is located between the split, or juncture of Outputs P and V and the one-way valve located in Output V. This second one-way directional valve provides for the release to atmosphere of only positive pressure, thus providing positive pressure exhaust.

In another embodiment, the negative pressure output of Output V to the express kits is provided with a pressure regulator for user control of Output V, which is the negative pressure (vacuum) to the express kits.

In a further embodiment, a filter is located between the air circuit and the pump, to protect the pump from contamination. A second filter can be located between the Output V of the air circuit and the vacuum input of the express kit. At least the first filter is preferably substantially permeable to air when the filter is dry or wet, and substantially impermeable to liquid.

BRIEF DESCRIPTION OF THE DRAWINGS

The above mentioned and other features of this invention and the manner of obtaining them will become more apparent, and the invention itself will be best understood by reference to the following description of an embodiment of the invention taken in conjunction with the accompanying drawings, in which.

DETAILED DESCRIPTION

Figure 1:
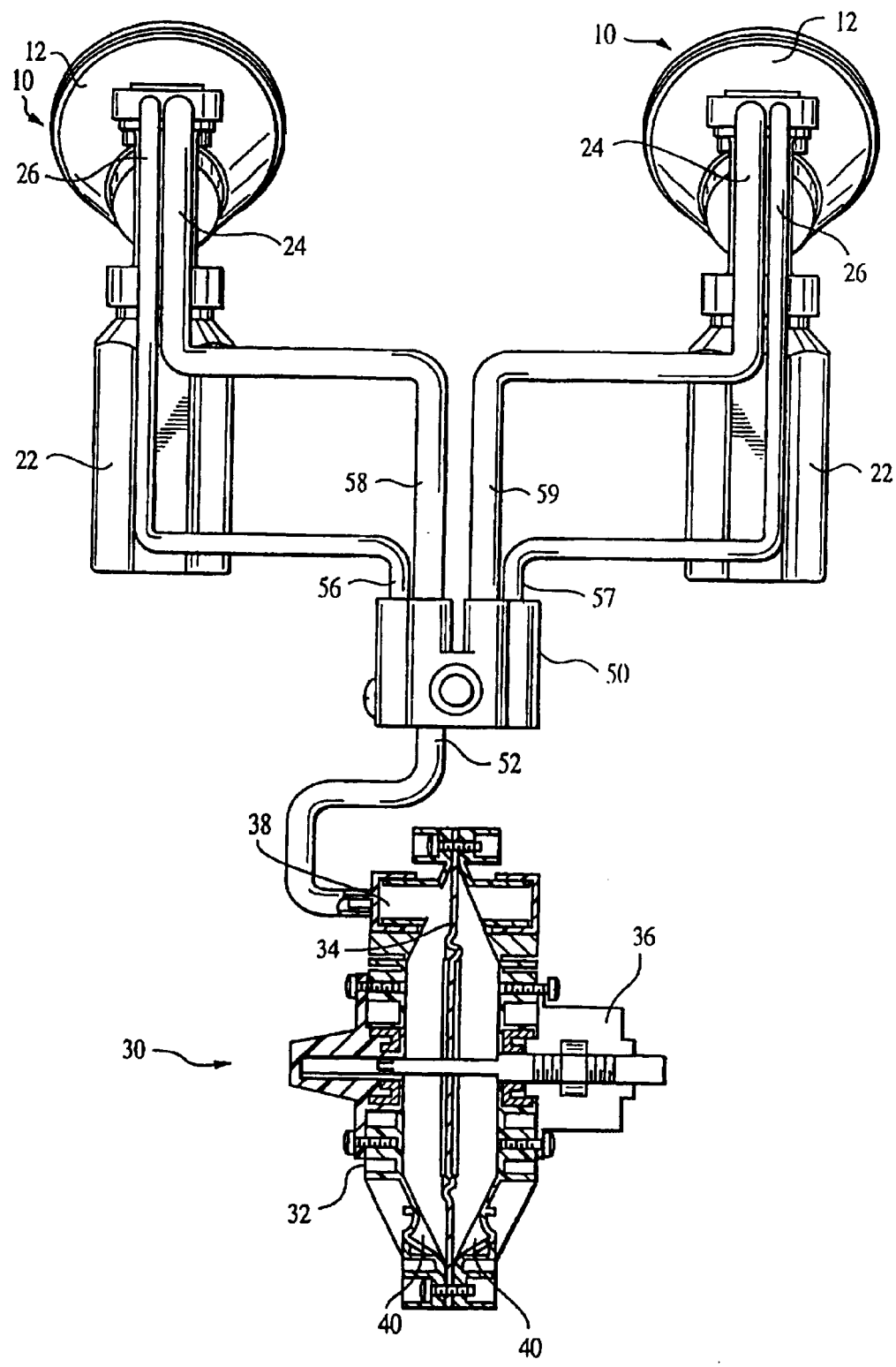
FIG. 1 illustrates an air circuit made in accordance with the present invention, connected to a pump and two express kits.
Figure 2:
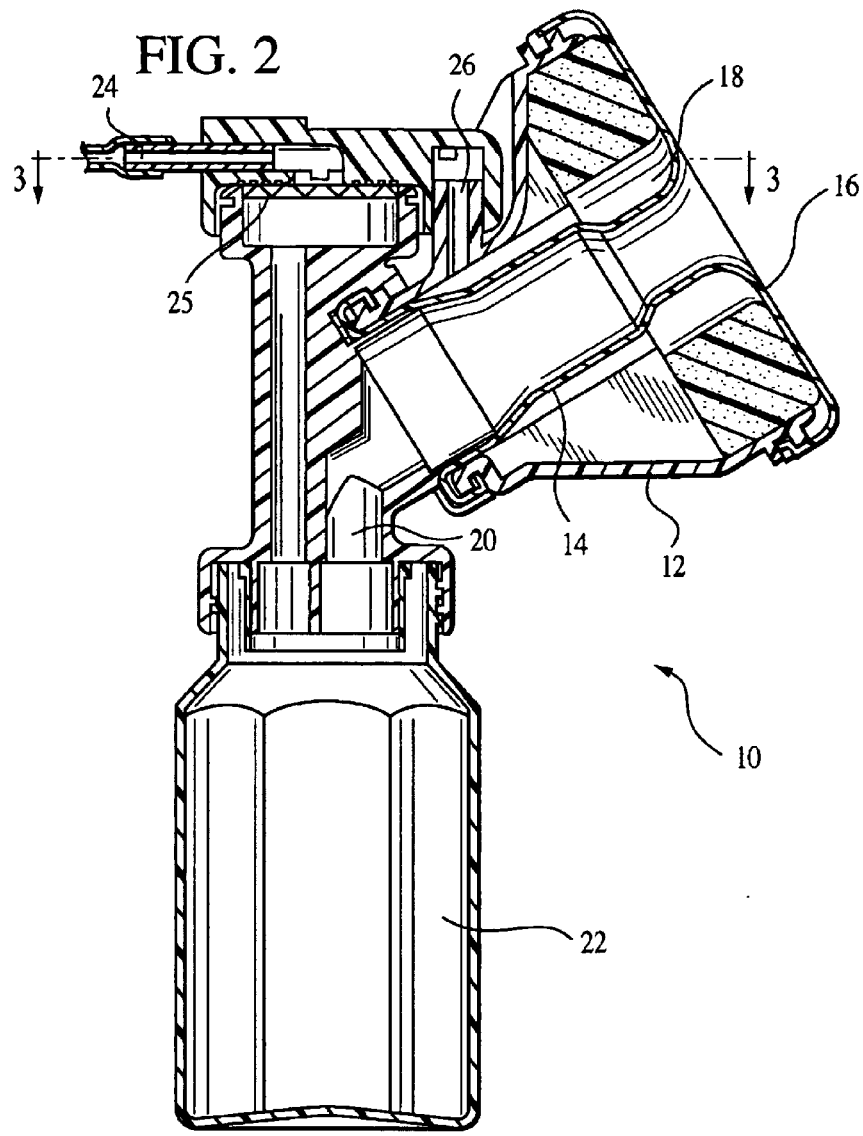
FIG. 2 is a partially cut-a-way plan view of an express kit for use with the present invention.
Figure 3:
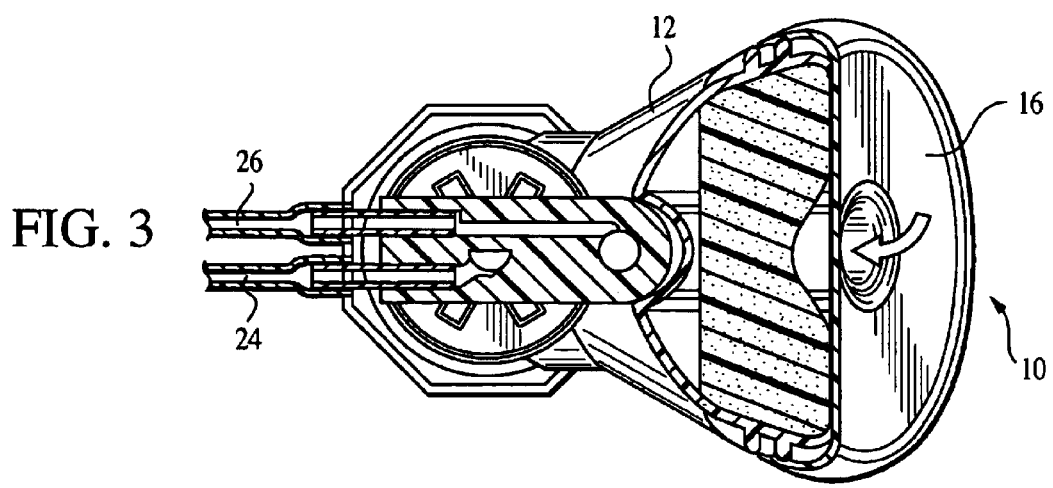
FIG. 3 is a partially cut-a-way top view of the express kit of FIG. 2, taken along lines 3—3 in FIG. 2.
Figure 4:
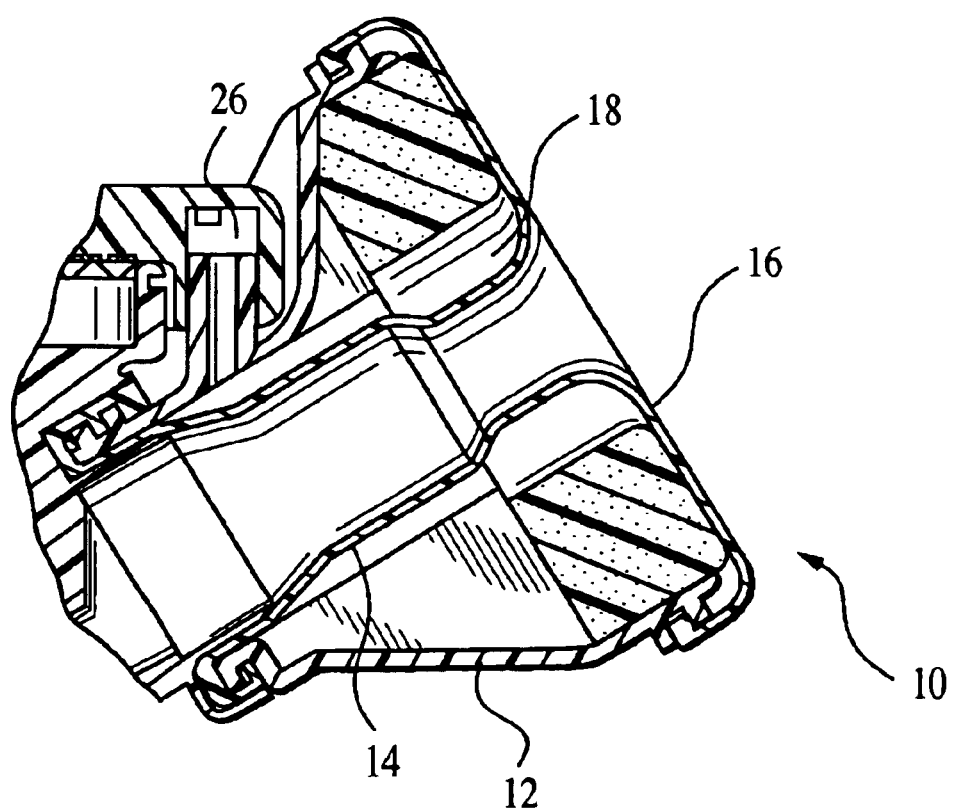
FIG. 4 is a cut-a-way view of the breast cup of FIG. 2, showing the liner in a collapsed condition.

As seen in FIGS. 1 through 4, a pair of breast cup (express) kits 10 each include a cup 12 and a liner 14. The liner 14 is secured on both ends of the cup to form a breast chamber 16 (when a breast is inserted into the cup) and a pulsation chamber 18. An outlet 20 is provided to remove milk expressed from the breast and deposit the milk in a collector 22.

The milk is drawn from the breast by a vacuum provided at an inlet 24. A filter 25 may be provided, if desired, to prevent or reduce contamination of the pump, which will be described. The filter 25 may be any suitable device, but is preferably substantially permeable to air when the filter is dry or wet, and substantially impermeable to liquid.

Pulsating pressure is applied to the pulsation chamber 18 through a pulsation input 26. The pulsating pressure is intermittently negative, or bi-directional. The pulsation pressure, in combination with the vacuum pressure applied to the breast in the breast chamber, opens and closes the pulsation chamber via the liner, modulating vacuum exposure to the breast, and providing massage to the breast.

Figure 6B:
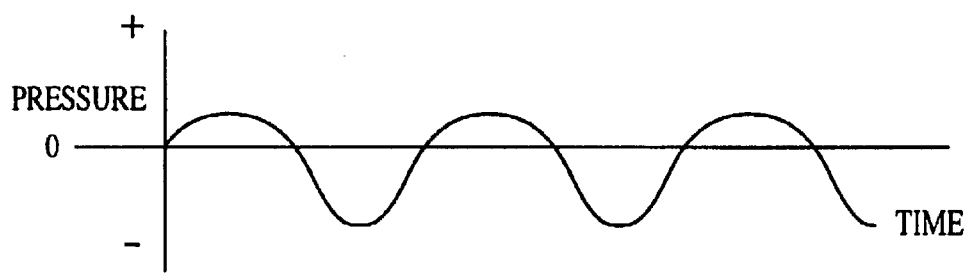
FIG. 6B is a graph of the pressure at the output of the pump of FIG. 6A.
Figure 7B:
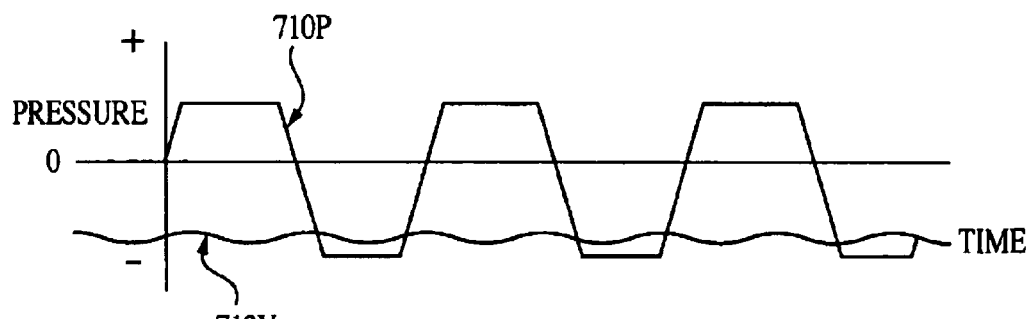
FIG. 7B is a graph of the pressures at the outputs of the pump of FIG. 7A.
Figure 6A:
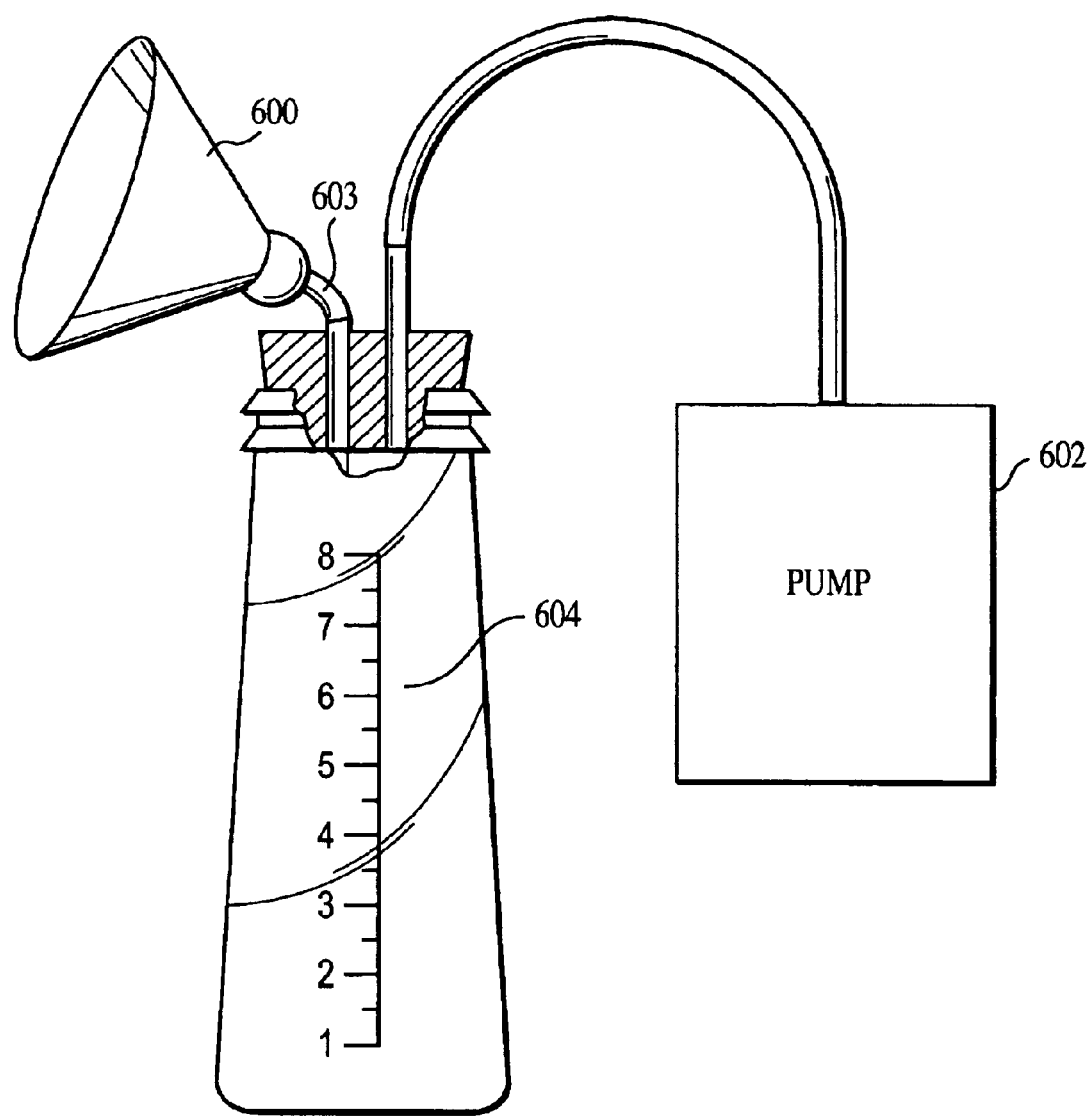
FIG. 6A is a diagram of a conventional breast pump, operated by a single source vacuum pressure.
Figure 7A:
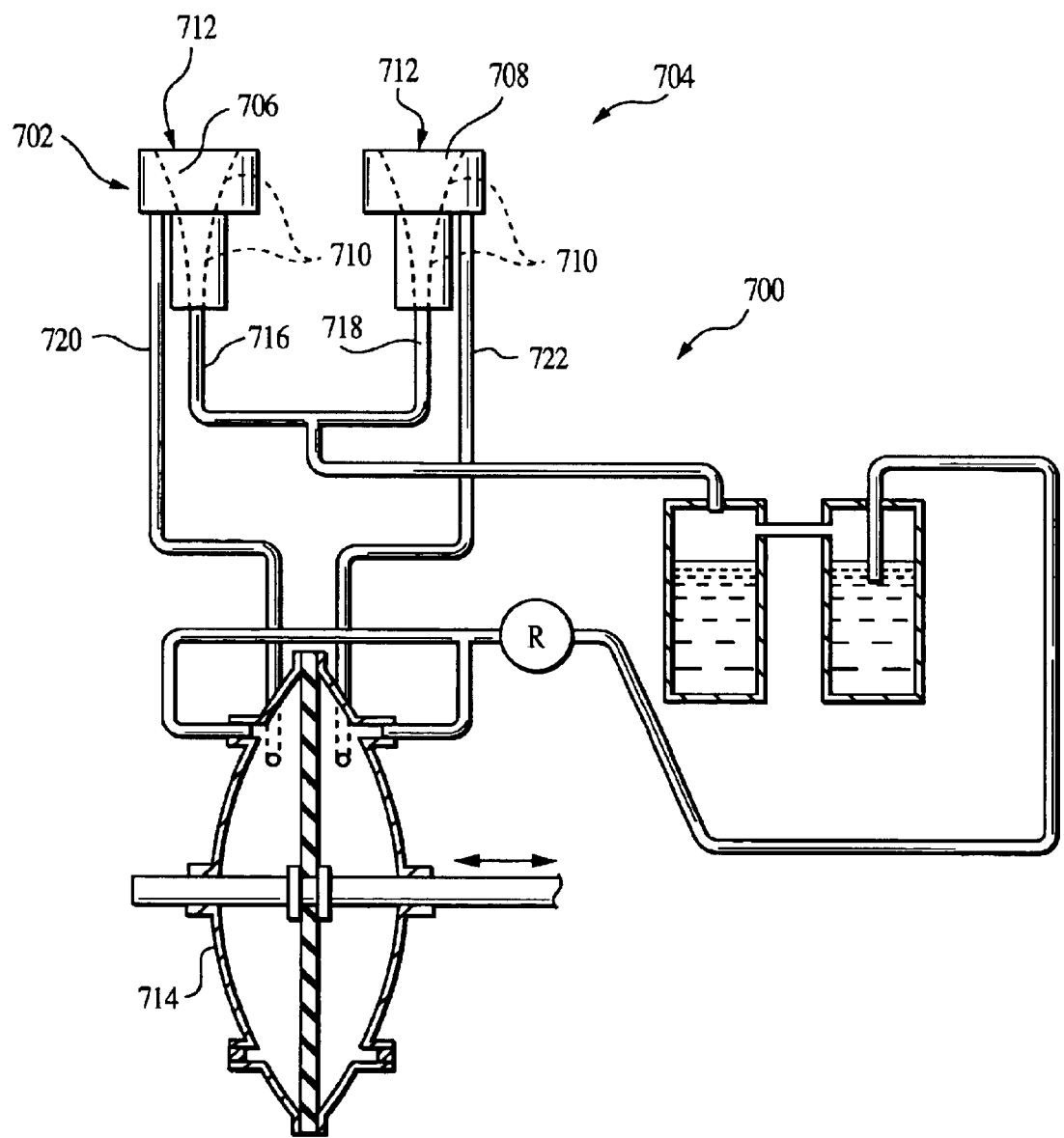
FIG. 7A is a diagram of another conventional breast pump, having lined breast cups and two sources of pressure.

The express kits 10 are operated by a pump 30. The pump 30 can be any suitable type of pump, such as the diaphragm pump shown. The pump 30 includes a housing 32, a diaphragm 34 in the housing and a motor 36 connecting the output of the motor to the diaphragm so that the diaphragm moves back and forth as the motor rotates. The pump produces bi-directional pressure (as in FIG. 6B) at a port 38 as the diaphragm reciprocates. Pressure can be vented through valves 40 as needed. The pump could also be a piston pump or other suitable pump, and it could be hand operated, if desired.

An air circuit 50 converts the vacuum output of the motor 30 into two outputs suitable for the express kits 10. The air circuit can be designed for use with one breast cup, or two breast cups, as in FIGS. 1 and 5A.

The air circuit 50 (FIG. 5A) includes an input 52 that feeds a one-way valve 54 through a chamber 55. A filter 53 may be placed in the input path, if desired, to protect against contamination. The output of the one-way valve 54 in turn feeds a first output 56, and a second output 57 (outputs V) when two breast cup assemblies are used. One output 56 or 57 could be plugged or eliminated if a single breast cup assembly were used. Filters 60 are used, if desired.

The outputs 56, 57 are re-arranged in FIG. 5, as compared with FIG. 1. This is easily accomplished using plastic tubing to interconnect various components of the air circuit.

The input 52 also feeds a third output 58 and a fourth output 59 (outputs P) through the chamber 55. The chamber 55 has a one-way check valve 62 that exhausts positive pressure as needed.

Pressure at the input 52 is bi-directional, i.e., both positive (pressure) and negative (vacuum), or intermittently negative, and it is transmitted directly to the outputs 58, 59 when two breast cup assemblies are used. A single breast cup configuration would only need one output 58 or 59. The valve 54 converts the bi-directional or intermittent pressure at the input 52 into a uni-directional vacuum. A vacuum reserve chamber 64 can be provided, if desired, as can a vacuum control valve 66. The valve 66 can be a needle valve or other suitable device that provides vacuum adjustment.

Figure 5A:
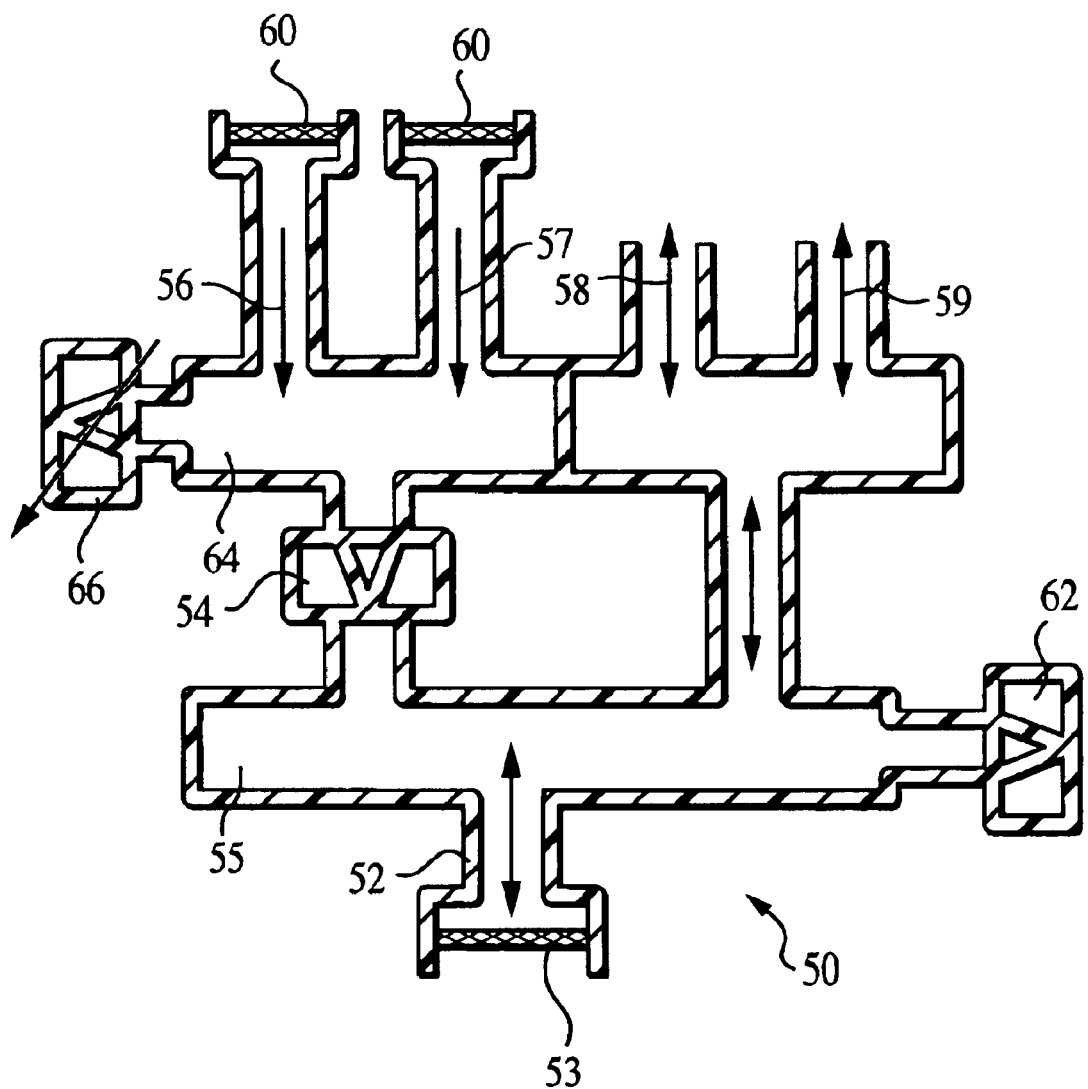
FIG. 5A is a diagram of the air circuit of the present invention.
Figure 5B:
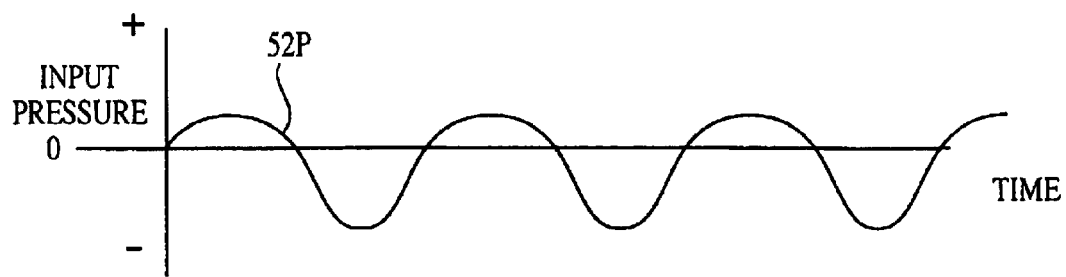
FIG. 5B is a graph of the pressure at the input of the air circuit of FIG. 5A.

In use, the pump 30 (FIG. 1) produces a bi-directional output which is fed to the input 52 (FIG. 5A). The pressure seen at the input 52 is shown as the line 52P in FIG. 5B. While many pressure curves would produce acceptable bi-directional pressure, a portion of each pressure cycle is preferably positive, and a portion of the cycle is negative, producing vacuum. The curve need not be symmetrical about the zero pressure line, and may have a stronger negative component, as in FIG. 5B. The pressure can be intermittent instead of bi-directional, if desired, though some discontinuity should be present, and a vacuum should be drawn somewhere in the cycle.

Figure 5C:
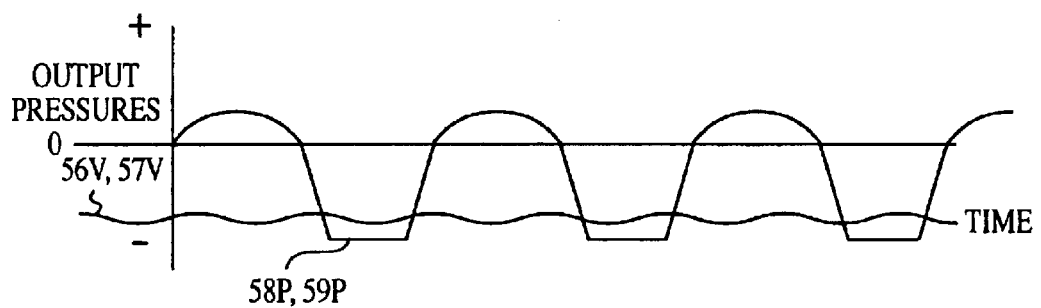
FIG. 5C is a graph of the pressures at the outputs of the air circuit of FIG. 5A.

The unidirectional pressure produced at the outputs 56, 57 of the air circuit 50 is shown in line 56V, 57V in FIG. 5C. While the vacuum is substantially constant, it can include some variation.

The bi-directional outputs produced at ports 58, 59 are shown in line 58P, 59P in FIG. 5C. These outputs massage the breast.

While the principles of the invention have been described above in connection with specific apparatus and applications, it is to be understood that this description is made only by way of example and not as a limitation on the scope of the invention.

What is claimed is:

1. An air circuit for a pump that produces bi-directional or intermittent negative air pressure and at least one express kit that requires either bi-directional or intermittent negative air pressure and unidirectional negative air pressure, the express kit having a breast cup, a liner in the breast cup and a milk collection device, the liner and breast cup forming a pulsation chamber that receives the air pressure, the liner and breast forming a vacuum chamber that receives the vacuum, the air circuit comprising:

an inlet for connection to the pump;

at least one first output providing from the inlet a bi-directional or intermittent negative air pressure output for the pulsation chamber; and at least one second output producing from the inlet a unidirectional vacuum for the vacuum chamber.

2. The air circuit of claim 1, comprising a one-way valve that converts the air pressure of the pump into the vacuum of the second output.

3. The air circuit of claim 1, comprising a check valve that exhausts positive pressure from the inlet as needed.

4. The air circuit of claim 1, comprising a vacuum control valve.

5. The air circuit of claim 1, comprising a filter in the inlet, for preventing contamination.

6. The air circuit of claim 1, comprising a filter in the second output.

7. The air circuit of claim 1, comprising two express kits.

* * * * *